United States Patent [19]
Winston et al.

[11] Patent Number: 5,951,482
[45] Date of Patent: Sep. 14, 1999

[54] ASSEMBLIES AND METHODS FOR ADVANCING A GUIDE WIRE THROUGH BODY TISSUE

[75] Inventors: Thomas R. Winston, Leawood; John M. Neet, Lawrence, both of Kans.

[73] Assignee: Intraluminal Therapeutics, Inc., Carlsbad, Calif.

[21] Appl. No.: 08/943,386

[22] Filed: Oct. 3, 1997

[51] Int. Cl.$^6$ .................................................. A61B 6/00
[52] U.S. Cl. .................. 600/476; 600/342; 600/478; 356/345
[58] Field of Search ................................. 600/476, 478, 600/433, 434, 342, 407, 473; 606/2, 3, 10, 15; 356/345

[56] References Cited

U.S. PATENT DOCUMENTS

| | | |
|---|---|---|
| 5,178,153 | 1/1993 | Einzig . |
| 5,293,872 | 3/1994 | Alfano et al. . |
| 5,411,551 | 5/1995 | Winston et al. . |
| 5,549,114 | 8/1996 | Petersen et al. . |
| 5,582,171 | 12/1996 | Chornenky et al. . |
| 5,601,087 | 2/1997 | Gunderson et al. . |
| 5,710,630 | 1/1998 | Essenpreis et al. . |

*Primary Examiner*—Brian L. Casler
*Assistant Examiner*—Shawna J Shaw
*Attorney, Agent, or Firm*—Armstrong Teasdale LLP; Scott R. Hayden

[57] ABSTRACT

Systems and methods for advancing a guide wire through body tissue are described. In one form, the guide wire includes an interferometric guidance system and a tissue removal member. The interferometric guidance system is coupled to the guide wire and includes a first optic fiber, a second optic fiber, and a detecting element. The first optic fiber includes a first end and a second end, and extends through a guide wire bore so that the second end is adjacent the guide wire second end. The second optic fiber of the guidance system similarly includes a first end and a second end, and a reference mirror is positioned adjacent the second optic fiber second end. The detecting element is configured to determine interference between a light beam propagating through the first optic fiber and a light beam propagating through the second optic fiber. The tissue removal member also is coupled to the guide wire and is configured to create a path through body tissue so that the guide wire may be advanced therethrough. A treatment laser to ablate tissue may also be used to open a channel through the plaque. A guide wire or centering catheter may be used to facilitate this maneuver.

28 Claims, 2 Drawing Sheets

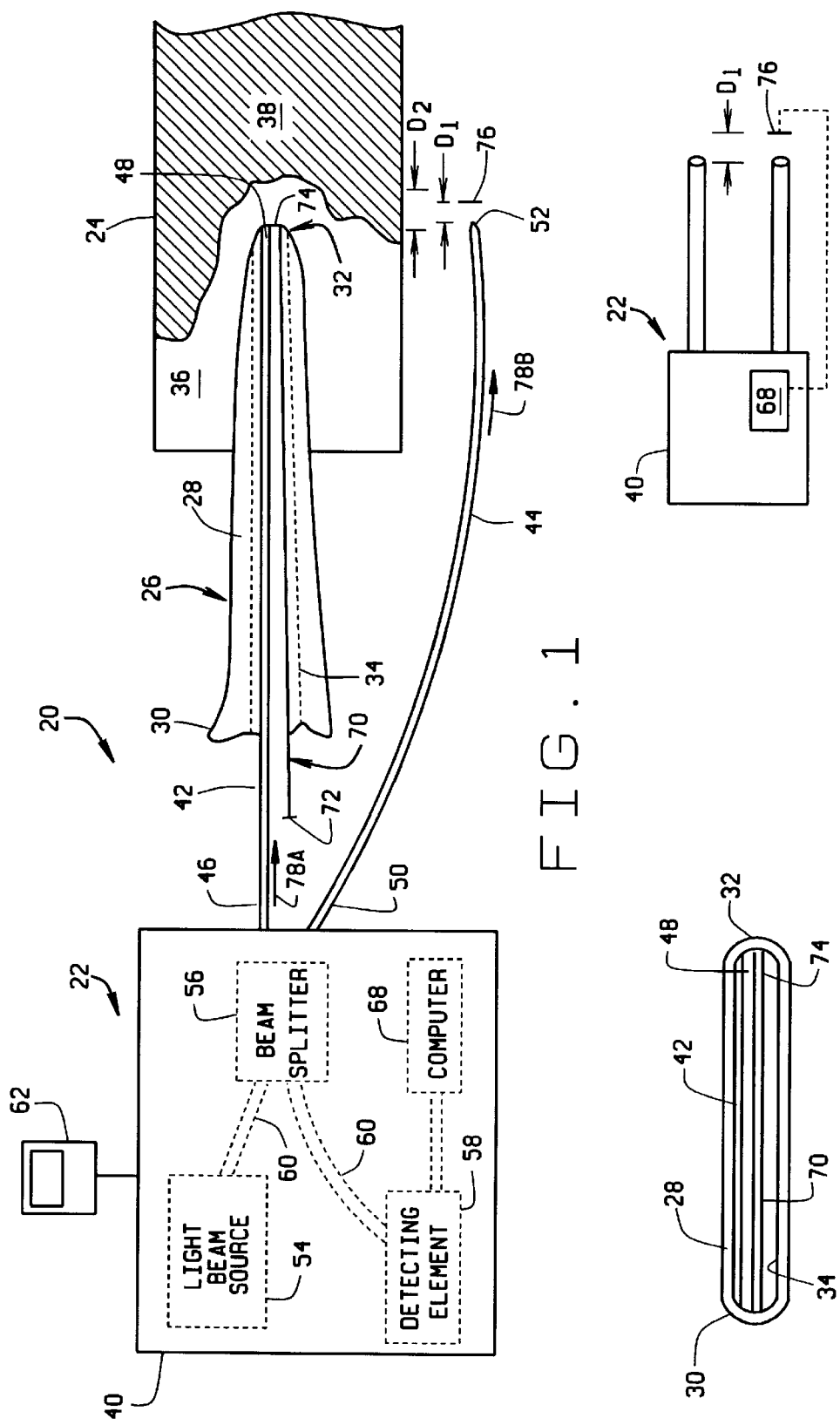

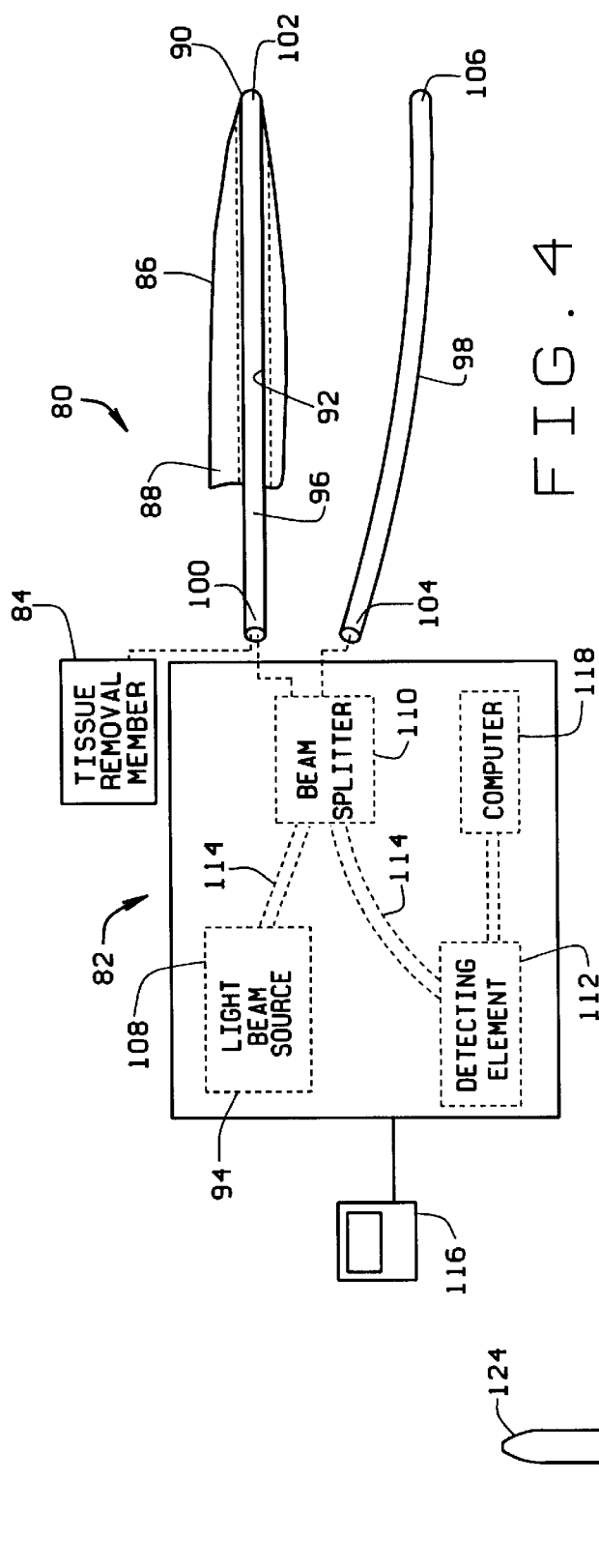
FIG. 4
FIG. 5
FIG. 6

ASSEMBLIES AND METHODS FOR ADVANCING A GUIDE WIRE THROUGH BODY TISSUE

FIELD OF THE INVENTION

This invention relates generally to medical guide wires and, more particularly, to assemblies and methods for advancing guide wires through body tissue.

BACKGROUND OF THE INVENTION

Disease processes, e.g., tumors, inflammation of lymph nodes, and plaque build-up in arteries, often afflict the human body. As one specific example, atherosclerotic plaque is known to build-up on the walls of arteries in the human body. Such plaque build-up restricts circulation and often causes cardiovascular problems, especially when the build-up occurs in coronary arteries. Accordingly, it is desirable to detect plaque build-up and remove or otherwise reduce such plaque build-up.

To treat such disease, it often is necessary to insert a medical device into the body, and to guide the medical device to the diseased site. Once the medical device is adjacent the diseased site the medical device typically is used to treat the diseased area.

Often a guide wire is used to help guide other treatment devices to this area. A guide wire typically is required to properly position a catheter in the artery. The guide wire is advanced through the artery and region of plaque build-up so that it forms a path through the artery and plaque build-up. The catheter or other device such as a balloon or rotational atherectomy device is then guided through the artery using the guide wire.

Known guide wires implement laser energy to remove plaque build up on artery walls for totally occluded arteries. One known catheter includes a laser source and a guide wire body. The guide wire body has a first end and a second end, or head, and several optical fibers extend between the first end and the second end. The laser source is coupled to each of the optical fibers adjacent the catheter body first end and is configured to transmit laser energy simultaneously through the optical fibers.

To remove arterial plaque, for example, the guide wire body is positioned in the artery so that the second end of the guide wire body is adjacent a region of plaque build-up. The laser source is then energized so that laser energy travels through each of the optical fibers and substantially photoablates the plaque adjacent the second end of the catheter body. The guide wire body is then advanced through the region to photoablate the plaque in such region.

It often is not feasible to insert known guide wires into an artery. For example, known guide wires typically cannot be extended through totally occluded arteries. Particularly, known guide wires are configured to be extended through paths already existing in a partially occluded artery. If such paths do not exist, e.g., if the artery is totally occluded, the guide wire may not be able to be advanced.

Accordingly, it would be desirable to provide a guide wire configured to be advanced through a totally occluded artery. It also would be desirable for such guide wire to be configured to provide imaging capability as well as the ability to open a small channel accurately through a totally occluded passage way.

SUMMARY OF THE INVENTION

These and other objects are attained by a guide wire which, in one embodiment, includes an interferometric guidance system and a tissue removal member. Particularly, the guide wire is substantially cylindrical and includes a first end, a second end, or guide wire head, and a bore extending between the first and second ends. The interferometric guidance system is coupled to the guide wire and includes a first optic fiber, a second optic fiber, and a detecting element. The first optic fiber includes a first end and a second end, and extends through the guide wire bore so that the second end is adjacent the guide wire second end. The second optic fiber of the guidance system similarly includes a first end and a second end, and a reference mirror is positioned adjacent the second optic fiber second end.

The detecting element is communicatively coupled to both the first optic fiber and the second optic fiber. Particularly, the first optic fiber first end is communicatively coupled to the detecting element and the second optic fiber first end is communicatively coupled to the detecting element. The detecting element is configured to determine interference between substantially equal light beams which are emitted from the same source and which are split to propagate through the first optic fiber and through the second optic fiber. The interference is then utilized to determine the density and type of tissue adjacent the guide wire head, and to advance the guide wire through the tissue.

The tissue removal member can be a second treatment laser sent down the same fiber optic inside the guide wire and could for example be an excimer laser. Similarly, in another embodiment, the fiber can be removed and a metal wire can be placed through the hollow channel extending beyond it to pick its way through the plaque. Either of these is coupled to the guide wire and includes a first end and a second end. The tissue removal member extends through the guide wire bore so that the second end of the tissue removal member is adjacent the guide wire head.

In operation, the guide wire is inserted at least partially into a blood vessel so that the guide wire head and the first optic fiber second end of the guidance system is positioned in the blood vessel. The second optic fiber is positioned outside the blood vessel, and the reference mirror is positioned a desired, or measuring, distance from the second optic fiber second end.

With respect to the detecting element, a light beam is split into first and second substantially equal light beams which are then transmitted through the first and second optic fibers, from their respective first ends to their respective second ends. The first light beam transmitted through the first optic fiber exits from the first optic fiber second end, is at least partially reflected by the tissue, re-enters the first optic fiber second end and propagates toward the first optic fiber first end. Similarly, the second light beam transmitted through the second optic fiber exits from the second optic fiber second end, is at least partially reflected by the reference mirror, re-enters the second optic fiber second end and propagates toward the second optic fiber first end.

The detecting element detects interference between the respective reflected first light beam and the reflected second light beam and transmits interference data to a computer. The computer then utilizes the interference data to determine the density and the type of the tissue to be examined adjacent the guide wire head. Particularly, the interference data is representative of the density and type of tissue located at the measuring distance from the first optic fiber second end, and the computer utilizes such data to generate an image of such tissue at such location. The computer also utilizes the interference data to control subsequent advancement of the guide wire through the artery.

In one embodiment, a fiber optic extends down the center of a conventional guide wire, and the guide wire may be guided through a total occluded artery. This guide wire may also be made with a harder (hardened steel) and less floppy end to make it more suitable to go through a totally occluded artery. The guide wire front end may also be made more sharp than known guide wires to facilitate it going through a totally occluded artery. Such a guide wire can be used to notify an operator when the wire gets too close to the normal arterial wall so that the operator can stop pushing ahead. Such detection is performed using light interferometric measurement to determine the interface between plaque and the media of the arterial wall. When the distance between the plaque and the more normal artery is noted at a predetermined distance then an indicator is used to notify the operator that a change should be made in how the guide wire is being manipulated so that the wire will go a different pathway. The wire may be fabricated so that it can be bent at its tip so that it can be "directed" down an artery.

This guide wire may also include a thin metal wire positioned next to the fiber optic which can be pulled back making the guide wire end very floppy. The metal wire, when extended, stiffens the more distal portion of the guide wire to facilitate moving through hardened plaque. This inner metal wire may similarly be able to be pushed beyond the tip of the guide wire through very hard plaque, and the guide wire then follows the metal wire onto its course down the plaque as long as the distal interferometry fiber can be certain the small wire is going down a safe pathway.

The guide wire may also be placed within a guiding sheath which stiffens the floppy tip of the guide wire to penetrate the plaque. The guide catheter may be placed on the guide wire if it becomes stuck in a plaque to facilitate either movement forward or backward. This guide catheter may have a balloon near the tip to facilitate centering the catheter in the artery, or an angioplasty balloon, and move in a stepwise fashion through the plaque. Specifically, the guide wire can be pushed through the plaque and followed with the balloon tipped guide catheter until it is through the lesion. The balloon can then be inflated to further dilate the plaque and enlarge the channel. Once the guide wire is through the blockage of the artery then laser angioplasty or atherectomy, conventional angioplasty, or rotational atherectomy may be done using this guide wire.

In yet another embodiment, the guide wire may be a conventional guide wire with the guiding catheter (with or without a balloon or using a balloon angioplasty device) and having the light interferometry fiber optic be part of the catheter guide or balloon angioplasty device to provide imaging feedback for guiding the tip of the guide wire.

If the interference data indicates a total occlusion, the tissue removal member is utilized to create a path through such occlusion, e.g., a treatment laser energy is sent simultaneously or separately down the same optic fiber. Particularly, the tissue removal member is extended from the guide wire head to remove tissue adjacent the guide wire head and create a path through which the guide wire may be advanced.

The above described guide wire is believed to be advancable through a totally occluded artery. Such guide wire also provides improved image accuracy as compared to known guide wires.

BRIEF DESCRIPTION OF THE DRAWINGS

FIG. 1 is a pictorial illustration of a guide wire assembly in accordance with one embodiment of the present invention inserted into a blood vessel.

FIG. 2 is a partial cross section view of the guide wire shown in FIG. 1.

FIG. 3 is a schematic illustration of the guidance system shown in FIG. 1.

FIG. 4 is a pictorial illustration of a tissue removal member in accordance with another embodiment of the present invention.

FIG. 5 is a pictorial illustration of a guide wire and tissue removal member in accordance with another embodiment of the present invention.

FIG. 6 is a pictorial illustration of the tissue member shown in FIG. 5 inserted into the guide wire when bent. This member may be straight or bent at any curvature depending upon the operator's desire.

DETAILED DESCRIPTION

FIG. 1 is a pictorial illustration of a guide wire assembly 20 including an interferometric guidance system 22 in accordance with one embodiment of the present invention inserted into a blood vessel 24 of a body. Guide wire assembly 20 includes a control element 26 and a guide wire 28. Guide wire 28 has a first end 30 and a head 32, and includes a bore 34 extending between first end 30 and head 32. Guide wire first end 30 is communicatively coupled to control element 26 and guide wire second end 32 is positioned within an interior 36 of blood vessel 24 adjacent tissue through which guide wire 28 is to be advanced, e.g., plaque 38. Guide wire 28 may be formed, for example, with a coiled wire.

Guidance system 22 includes a control element 40, a first, or measuring, optic fiber 42, and a second, or reference, optic fiber 44. First optic fiber 42 includes a first end 46 and a second end 48, and is coupled to guide wire 28 so that second end 48 is adjacent guide wire head 32 and is positioned in blood vessel interior 36. Second optic fiber 44 also includes a first end 50 and a second end 52. First optic fiber first end 46 and second optic fiber first end 50 are communicatively coupled to system control element 40.

First optic fiber 42 is configured to emit energy waves substantially coaxially with respect to guide wire head 32. Alternatively, second end 48 of first optic fiber 42 may include a prism (not shown in FIG. 1) and be configured to emit an energy beam at an angle with respect to guide wire head 32, e.g., perpendicularly with respect to optic fiber 42.

Guidance system control element 40 includes a diagnostic light beam source 54, a beam splitter 56, and a detecting element 58. Beam splitter 56 is communicatively coupled to first optic fiber first end 46 and to second optic fiber first end 50. Beam splitter 56 also is coupled to diagnostic light beam source 54 and detecting element 58 via optic fibers 60.

Detecting element 58 further is coupled to an image screen 62 and is configured to transmit image data to image screen 62 for displaying an image or a psuedo image of the tissue to be imaged. Detecting element 58 also is configured to transmit control data to guide wire control element 26. Particularly, detecting element 58 is configured to determine interference between a light beam propagating through first optic fiber 42 and a light beam propagating through second optic fiber 44, and to generate interference data representative of such interference. For example, detecting element 58 may include a detector, a demodulator and an analog digitizer which cooperate in a known manner to generate such interference data. Such interference data is transmitted to a computer 64 which generates image data for display on image screen 62 and generates control data for transmission to guide wire control element 26 or to notify the operator if being operated by hand of an adverse situation and to discontinue pursuing the current path.

Guide wire assembly 20 may optionally further include a tissue removal member 70 coupled to guide wire 28. Tissue removal member 70 is, for example, a wire, and includes a first end 72 and a second end 74. Tissue removal member 70 extends through the guide wire bore so that second end 74 is adjacent the guide wire head 32. First end 72 is movably coupled to guide wire 28 to extend and retract tissue removal member 70 from guide wire head 32. Tissue removal member 70 may also be utilized to vary the floppiness, or stiffness, of guide wire 28.

As shown more clearly in FIG. 2, guide wire bore 34 extends between guide wire first and second ends 30 and 32, respectively. First optic fiber 42 extends through guide wire bore 34 so that second end 48 of first optic fiber 42 is adjacent guide wire head 32. Similarly, tissue removal member 70 extends through guide wire bore 34 so that second end 74 of tissue removal member 70 is adjacent guide wire head 32.

Referring now to FIG. 3, guidance system 22 further includes a reference mirror 76 positioned adjacent second fiber second end 52. Reference mirror 76 is movable with respect to second fiber second end 52 and is controlled, for example, by computer 68.

Prior to inserting guide wire assembly 20 into blood vessel 24, guidance system 22 is calibrated. Particularly, reference mirror 76 is positioned a distance $D_1$ from second fiber second end 52 and guidance system 22 is calibrated so that interference data obtained by detecting element 58 is representative of tissue located approximately the same distance $D_1$ from first optic fiber second end 48.

Referring again to FIG. 1, and after calibrating guidance system 22, guide wire assembly 20 is inserted into blood vessel 24 so that guide wire head 32 and first optic fiber second end 48 is positioned within blood vessel 24, and second optic fiber second end 52 is positioned outside blood vessel 24, and outside the body. Reference mirror 76, as explained above, is positioned distance $D_1$ from second optic fiber second end 52.

Light beam source 54 transmits a diagnostic light beam to beam splitter 56, which splits the light beam into first and second substantially equal light beams 78A and 78B, respectively. First light beam 78A is then transmitted through first optic fiber 42 and second light beam 78B is transmitted through second optic fiber 44. First light beam 78A exits from first optic fiber second end 48 substantially coaxially with respect to guide wire head 32, is at least partially reflected by the tissue, re-enters first optic fiber second end 48 and propagates toward first optic fiber first end 46. Similarly, second light beam 78B transmitted through second optic fiber 44 exits from second optic fiber second end 52, is at least partially reflected by reference mirror 76, re-enters second optic fiber second end 52 and propagates toward second optic fiber first end 50.

Detecting element 58 detects light interference patterns, e.g., interferences, between the reflected first light beam 78A and reflected second light beam 78B, and transmits interference data representative of such interferences to computer 68. Computer 68 utilizes the interference data to determine the type and depth of the tissue located at a distance $D_2$ from first optic fiber second end 48. Particularly, computer 68 utilizes the interference data to determine what type of tissue, if any, is located at a distance $D_2$ from first fiber second end 48, where distance $D_2$ is substantially the same as distance $D_1$. For example, computer 68 may include a memory, and representative interference signals for different types of tissues, e.g., plaque, no tissue, artery walls, healthy tissue, cancerous tissue, may be stored in such memory. Computer 68 compares the interference data received from detecting element 58 to such stored representative interference signals to determine the type of tissue located distance $D_2$ from first fiber second end 48. Distances $D_1$ and $D_2$ may, for example, be less than or equal to 1 millimeter, e.g., one quarter of a millimeter. Of course, distances $D_1$ and $D_2$ may be larger than 1 millimeter.

If desired, reference mirror 76 may be moved with respect to second fiber second end 48 to recalibrate guidance system 22 while it is positioned in a blood vessel 24. Particularly, if detecting element 58 generates interference data representative of a loss of signal through first optic fiber 42, reference mirror 76 may be moved to reestablish a signal at a distance $D_3$ (not shown in FIG. 1) which is different from distance $D_1$.

Similarly, and in yet another alternative, reference mirror 76 may be moved with respect to second fiber second end 48 to determine the type and depth of the tissue located at varying distances from second fiber second end 48. Particularly, reference mirror 76 may be moved between a point immediately adjacent second fiber second end 48 and a point distance $D_1$ from second fiber second end 48 to determine the type and depth of the tissue located at each point between such two points. Accordingly, reference mirror 76 may be moved to determine tissue type at multiple different distances from second fiber second end 48.

Computer 68 generates image data of such tissue and displays the image of such tissue or a representative pseudo image on screen 62. Particularly, computer 68 utilizes the interference data generated at various points in the tissue to generate image data representative of a substantially linear image profile of the examined tissue. Computer 68 also may utilize the interference data to generate and transmit control signals to guide wire control element 26, as is described in more detail below. If an operator is controlling the guide wire by hand, the control signals will be provided to a monitor while the operator controls the guidance by hand.

If the tissue located at distance $D_2$ is, for example, plaque 38, e.g., if blood vessel 24 is fully occluded at distance $D_2$, then tissue removal member 70 may be utilized to create a path through such plaque 38. Particularly, second end 74 of tissue removal member 70 is extended from guide wire head 32 to remove plaque 38 adjacent guide wire head 32. For example, tissue removal member 70 may be spring mounted within guide wire bore 34 and ejected from guide wire head 32 with sufficient force to penetrate plaque 38 adjacent head 32. In one embodiment, spring mounted tissue removal member 70 is communicatively coupled to guide wire control element 26. If guide wire head 32 is adjacent a total occlusion, control element 26 transmits control signals to spring mounted tissue removal member 70 and actuates the spring to eject tissue removal member 70 from guide wire head 32. Alternatively, spring mounted tissue removal member 70 may be manually actuated. In still yet another alternative, tissue removal member 70 is not spring mounted, and operator, e.g., a surgeon, may manipulate tissue removal member 70 to scrap or otherwise pick through plaque 38 adjacent guide wire head 32.

To facilitate determining accurate tissue depth and tissue type during blood vessel 24 movement, e.g., if blood vessel 24 is located in the heart, where blood vessel 24 may move relative to guide wire head 32 even if guide wire head 32 is not advanced through blood vessel 24, guidance system 22 may be configured to determine tissue type and density at only periodic intervals. For example, if blood vessel 24 is located in the heart, and it is not practical to stop the heart, then computer 68 may be configured to sample interference data from respective detecting element 58 at a same period of time of the cardiac cycle. Particularly, computer 68 may be communicatively coupled to an EKG and configured to sample interference data only at the top of the R wave. Alternatively, computer 68 may be communicatively coupled to an EKG and configured to sample interference data only at the middle of the T wave. Of course, computer 68 may be configured to sample interference data at other periodic intervals.

Guide wire bore 34 may, for example, have a diameter of approximately 0.014 inches. First optic fiber 42 may, for example, have a diameter of approximately 0.004 inches. Tissue removal member 70 may, for example, have a diameter of approximately 0.002 to 0.004 inches.

The above described guide wire is believed to be advancable through a totally occluded artery. Such guide wire also provides improved image accuracy as compared to known guide wires utilizing ultrasound. However, it is to be understood that the above described guide wire was exemplary and that other embodiments are possible.

For example, in an alternative embodiment, guide wire assembly 20 includes two interferometric guidance systems coupled to the guide wire. Each interferometric guidance system is configured as described above with respect to guidance system 22. The first, or measuring, optic fibers of each such system extend through the guide wire bore so that their respective second ends are adjacent the guide wire head. The first optic fiber of one of the guidance systems is configured to emit energy waves substantially coaxially with respect to the guide wire head. The first optic fiber of the other guidance system includes a prism and is configured to emit an energy beam at an angle with respect to the guide wire head.

In yet another embodiment, the guide wire assembly includes only one guidance system 22. Particularly, the guide wire bore is sized to receive first optic fiber 42, but not sized to simultaneously receive tissue removal member 70.

In still yet another embodiment, the guide wire assembly includes only tissue removal member 70. Particularly, the guide wire bore is sized to receive tissue removal member 70, but not sized to simultaneously receive first optic fiber 42.

The above described guide wires are believed to be advancable through a totally occluded artery. Such guide wires also provides improved image accuracy as compared to known guide wires utilizing ultrasound.

For example, FIG. 4 is a pictorial illustration of a guide wire assembly 80 in accordance with another embodiment of the present invention. Guide wire assembly 80 includes an interferometric guidance system 82, a tissue removal member 84 and a guide wire 86. Guide wire 86 has a first end 88 and a rounded, or hemispherical, conical or other shape second end, or head, 90, and includes a bore 92 extending between first end 88 and head 90. Guide wire 86 may be fabricated, for example, with a coiled wire.

Guidance system 82 is configured the same as guidance system 22 and includes a control element 94, a first, or measuring, optic fiber 96. First optic fiber 96 includes a first end 100 and a second end 102, and is coupled to guide wire 86 so that second end 102 is adjacent guide wire head 90. Second optic fiber 98 also includes a first end 104 and a second end 106. First optic fiber first end 100 and second optic fiber first end 104 are communicatively coupled to system control element 94.

First optic fiber 96 is configured to emit an energy beam, e.g., a light beam, substantially coaxially with respect to guide wire head 90. Alternatively, second end 102 of first optic fiber 96 may include a prism (not shown in FIG. 1) and be configured to emit an energy beam at an angle with respect to guide wire head 90, e.g., perpendicularly with respect to optic fiber 96.

Guidance system control element 94 includes a diagnostic light beam source 108, a beam splitter 110, and detecting element 112. Beam splitter 110 is communicatively coupled to first optic fiber first end 100 and to second optic fiber first end 104. Beam splitter 110 also is coupled to diagnostic light beam source 108 and detecting element 112 via optic fibers 114.

Detecting element 112 further is coupled to an image screen 116 and is configured to transmit pseudo image data to image screen 116 for displaying an image of the normal and abnormal tissue and then interface. Detecting element 112 also is configured to transmit control data to the operator of the guide wire. Particularly, detecting element 112 is configured to determine interference between a light beam propagating through first optic fiber 96 and a light beam propagating through second optic fiber 98, and to generate interference data representative of such interference. For example, detecting element 112 may include a detector, a demodulator and an analog digitizer which cooperate in a known manner to generate such interference data. Such interference data is transmitted to a computer 118 which generates image data for display on image screen 116 and generates control data for transmission to guide wire control element 94.

Tissue removal member 84 is communicatively coupled to guide wire 86 and is configured to transmit a treatment energy beam through first optic fiber 96. Particularly, tissue removal member 84 includes a treatment energy source, e.g., a laser source, communicatively coupled, e.g., with mirrors, to first end 100 of first optic fiber 96 and configured to transmit a treatment energy beam through first optic fiber 96.

In operation, if interference data obtained by guidance system 82 indicates a total occlusion adjacent guide wire head 90, tissue removal member 84 is utilized to create a path through such occlusion. Particularly, tissue removal member 84 transmits a treatment energy beam through the first optic fiber 96 to photoablate plaque adjacent guide wire head 90 and create a path through which guide wire 86 may be advanced.

The above described guide wire assembly is advancable through a totally occluded artery. Such guide wire assembly also is steerable through a totally occluded artery. Moreover, such guide wire assembly is configured so that first optic fiber 96 of guidance system 82 may be utilized for both detecting tissue and photoablating through such tissue.

In still another embodiment, and referring now to FIGS. 5 and 6, a guide wire assembly includes a bendable guide wire 120 or tissue removal member 122 may be bent inside the guide wire 120 to make it angle or be straight. Guide wire 120 is bendable between a first position, where a second end 124 of guide wire 120 is substantially straight, and a second position, where second end 124 is substantially angled. Similarly, tissue removal member 122, e.g., a wire, is bendable between a first position, where a second end 126 of tissue removal member 122 is substantially straight, and a second position, where second end 126 is substantially angled. Tissue removal member 122, as described above with respect to tissue removal member 70, is configured to extend through a guide wire bore 128 and guide wire second end 124 between the first position and the second position.

In operation, guide wire second end 124 is maintained in its first position while being inserted into an artery. While advancing guide wire second end 124 through the artery, the artery may curve, in which case it may be desirable to bend guide wire second end 124. To bend guide wire second end 124, tissue removal member second end 126 is moved to its second position, e.g., an operator bends second end 126 of tissue removal member 122, and is extended through guide wire bore 128. When tissue removal member second end 126 is adjacent guide wire second end 124, tissue removal member 122 deforms guide wire second end 124 and results in guide wire second end 124 moving to its second position. Guide wire second end 124 is then advanced through the curved artery.

The tissue removal member 122 and guide wire 120 described above are believed to be steerable through body tissue more easily than known guide wires. In addition, such removal member 122 and guide wire 120 are advancable through a totally occluded artery. Guide wire 120 may have special hardened steel or sharp edges to facilitate it moving through totally occluded arteries.

Many other variations are contemplated and possible. For example, in another embodiment, a fiber optic may be extended down the center of a conventional guide wire, and the guide wire may be guided through a total occluded artery. This guide wire may also be made with a harder (hardened steel) and less floppy end to make it more suitable to go through a totally occluded artery. The guide wire front end may also be made more sharp than known guide wires to facilitate it going through a totally occluded artery. The wire may be fabricated so that it can be bent at its tip so that it can be "directed" down an artery.

The guide wire may also include a thin metal wire positioned next to the fiber optic which can be pulled back making the guide wire end very floppy. The metal wire, when extended, stiffens the more distal portion of the guide wire to facilitate moving through hardened plaque. This inner metal wire may similarly be able to be pushed beyond the tip of the guide wire through very hard plaque, and the guide wire then follows the metal wire onto its course down the plaque as long as the distal interferometry fiber can be certain the small wire is going down a safe pathway.

The guide wire may also be placed within a guiding sheath which stiffens the floppy tip of the guide wire to penetrate the plaque. The guide catheter may be placed on the guide wire if it becomes stuck in a plaque to facilitate either movement forward or backward. This guide catheter may have a balloon near the tip to facilitate centering the catheter in the artery, or an angioplasty balloon, and move in a stepwise fashion through the plaque. Specifically, the guide wire can be pushed through the plaque and followed with the balloon tipped guide catheter until it is through the lesion. The balloon can then be inflated to further dilate the plaque and enlarge the channel. Once the guide wire is through the blockage of the artery then laser angioplasty or atherectomy, conventional angioplasty, or rotational atherectomy may be done using this guide wire.

In yet another embodiment, the guide wire may be a conventional guide wire with the guiding catheter (with or without a balloon or using a balloon angioplasty device) and having the light interferometry fiber optic be part of the catheter guide or balloon angioplasty device to provide imaging feedback for guiding the tip of the guide wire.

It also is contemplated that spark gap cavitation can be used in connection with any of the above described embodiments. With spark gap cavitation, and as known in the art, two prongs are electrified using an energy source to eliminate plaque.

From the preceding description of the present invention, it is evident that the objects of the invention are attained. Although the invention has been described and illustrated in detail, it is to be clearly understood that the same is intended by way of illustration and example only and is not be taken by way of limitation. Accordingly, the spirit and scope of the invention are to be limited only by the terms of the claims.

What is claimed is:

1. A guide wire assembly comprising:
   a guide wire having a first end, and a second end and a bore extending between said first end and said second end; and
   at least one guidance system coupled to said guide wire, said guidance system comprising a first optic fiber for propagating a sampling light beam, said first optic fiber having a first end and a second end, a second optic fiber for propagating a reference light beam, said second optic fiber having a first end and a second end, a reference mirror positioned adjacent said second optic fiber second end, and a detecting element communicatively coupled to said first ends of said first and second optic fibers, said first optic fiber coupled to said guide wire so that said first optic fiber second end is adjacent said second end of said guide wire, wherein said guide wire second end is configured to direct the sampling light beam substantially coaxially with respect to said guide wire second end, wherein said detecting element is configured to determine interference between the sampling light beam and the reference light beam, and wherein said guidance system is configured to determine the safety of advancing said guide wire second end a predetermined distance.

2. A guide wire assembly in accordance with claim 1 wherein said first optic fiber extends through said guide wire bore.

3. A guide wire assembly in accordance with claim 1 comprising two guidance systems, each said guidance system comprising a first optic fiber having a first end and a second end, each said first optic fiber extending through said guide wire bore so that said respective first optic fiber second ends are adjacent said guide wire second end.

4. A guide wire assembly in accordance with claim 3 wherein one of said first optic fibers is configured to emit an energy beam substantially coaxially with respect to said guide wire second end, and wherein said other of said first optic fibers is configured to emit an energy beam at an angle with respect to said guide wire second end.

5. A guide wire assembly in accordance with claim 4 wherein one of said first optic fibers comprises a prism adjacent its second end.

6. A guide wire assembly in accordance with claim 1 further comprising a tissue removal member coupled to said guide wire.

7. A guide wire assembly in accordance with claim 6 wherein said tissue removal member extends through said guide wire bore.

8. A guide wire assembly in accordance with claim 6 wherein said tissue removal member comprises a first end and a second end, and is configured to move between a first position, where said tissue removal member second end is adjacent said guide wire second end, and a second position, where said tissue removal member second end extends from said guide wire second end.

9. A guide wire assembly in accordance with claim 6 wherein said tissue removal member is spring mounted to said guide wire.

10. A guide wire assembly in accordance with claim 6 wherein said tissue removal member comprises a first end, a second end, and a portion adjacent said tissue removal member second end that can be manually manipulated to a desired configuration to help "aim" the guide wire.

11. A guide wire assembly in accordance with claim 1, said assembly further comprising balloon coupled to said guide wire for at least one of centering and angioplasty.

12. A guide wire assembly in accordance with claim 1, said assembly further comprising a tissue removal member coupled to said guide wire.

13. A guide wire assembly in accordance with claim 12 wherein said tissue removal member is positioned within said guide wire bore so that an end of said tissue removal member is adjacent said guide wire second end.

14. A guide wire assembly in accordance with claim 12 wherein said tissue removal member is configured to move between a first position, where said tissue removal member second end is adjacent said guide wire second end, and a second position, where said tissue removal member second end extends from said guide wire second end.

15. A guide wire assembly in accordance with claim 12 wherein said tissue removal member is spring mounted to said guide wire.

16. A guide wire assembly in accordance with claim 12 wherein said tissue removal member comprises a first end, a second end, and a curved portion positioned adjacent said tissue removal member second end.

17. A guide wire assembly in accordance with claim 12 further configured to display tissue planes between body tissues adjacent said guide wire second end.

18. A method for advancing a guide wire through a blood vessel utilizing at least one laser interferometric system for generating interference data, the guide wire including a first end, a second end, and a bore extending therebetween, each laser interferometric system including a first optic fiber, a second optic fiber, and a detecting element communicatively coupled to both the first optic fiber and the second optic fiber, said method comprising the steps of:

extending the first optic fiber of at least one laser interferometric system through the guide wire bore;

inserting the guide wire at least partially into the blood vessel; and utilizing the interference data to determine the safety of advancing the guide wire second end a predetermined distance.

19. A method in accordance with claim 18 wherein extending the first optic fiber of at least one laser interferometric guidance system through the guide wire bore comprises the step of extending the first optic fiber of a first laser interferometric system and the first optic fiber of a second laser interferometric guidance system through the guide wire bore.

20. A method in accordance with claim 18 wherein if the interference data indicates that plaque is present at the predetermined distance from the second end of the first optic fiber, said method further comprises the step of forming a path through the plaque.

21. A method in accordance with claim 20 wherein to form a path through the plaque, said method comprises the step of extending a tissue removal member through the guide wire bore so that the tissue removal member extends from the second end of the guide wire.

22. Guide wire apparatus comprising:

a guide wire having a first end and a second end;

an interferometry system coupled to said guide wire;

a laser treatment system coupled to said guide wire; and an optical fiber utilized by both said interferometry system and said laser treatment system, said optical fiber having a first end and a second end, said optic fiber coupled to said guide wire so that said optic fiber second end is adjacent said guide wire second end, wherein said interferometry system is configured to determine the safety of advancing said guide wire second end though a tissue at a predetermined distance from said second end of said optic fiber.

23. Guide wire apparatus comprising:

a guide wire having a first end and a second end;

an interferometry system coupled to said guide wire;

a laser treatment system coupled to said guide wire; and at least two optical fibers, said optical fibers each having a first end and a second end, at least one of said optical fibers utilized by said interferometry system and at least one of said optical fibers utilized by said laser treatment system, said at least one optical fiber utilized by said interferometric system coupled to said guide wire so that said second end of said optic fiber utilized by said interferomteric system is adjacent said guide wire second end, wherein said interferometry system is configured to determine the safety of advancing said guide wire second end though a tissue at a predetermined distance from said second end of said optic fiber utilized by said interferometric system.

24. Guide wire apparatus in accordance with claim 1, said apparatus further comprising an treatment energy source coupled to said guide wire.

25. Guide wire apparatus in accordance with claim 24, wherein said treatment energy source comprises a laser source for providing a laser beam, wherein said first optic fiber is utilized for propagating both the sampling beam and the laser beam.

26. Guide wire apparatus in accordance with claim 24 wherein said treatment energy source comprises a laser source for providing a laser beam, said laser source comprising a treatment optic fiber for propagating the laser beam, said treatment optic fiber extending through said guide wire bore.

27. Guide wire apparatus in accordance with claim 1 further comprising a balloon coupled to said guide wire.

28. Guide wire apparatus in accordance with claim 27 wherein said balloon comprises at least one of a centering balloon and an angioplasty balloon.

* * * * *